United States Patent [19]

Collins et al.

[11] Patent Number: 5,038,791

[45] Date of Patent: Aug. 13, 1991

[54] HEART IMAGING METHOD

[75] Inventors: H. Dale Collins; R. Parks Gribble, both of Richland, Wash.; Lawrence J. Busse, Littleton, Colo.

[73] Assignee: Battelle Memorial Institute, Richland, Wash.

[21] Appl. No.: 536,351

[22] Filed: Jun. 11, 1990

[51] Int. Cl.⁵ .............................................. A61B 5/044
[52] U.S. Cl. ................................................... 128/696
[58] Field of Search ............... 128/696, 699, 710, 712, 128/916, 660.001, 660.002, 665; 364/413.02, 413.06, 413.13, 413.19, 413.21

[56] References Cited

U.S. PATENT DOCUMENTS

| 4,074,564 | 2/1978 | Anderson | 364/413.019 |
| 4,182,316 | 1/1980 | Nilsson et al. | 128/665 |
| 4,531,411 | 7/1985 | Collins et al. | 73/603 |
| 4,594,662 | 10/1986 | Devaney | 128/916 |
| 4,680,709 | 7/1987 | Srinivasan et al. | 364/413.021 |
| 4,898,181 | 2/1990 | Kessler | 128/699 |

OTHER PUBLICATIONS

B. P. Hildebrand, A. J. Boland, M. L. Cochran, "Linear Impulse Holography" *Acoustical Imaging*, vol. 11, Plenum Press, New York, NY (1982), pp. 529–547.

*Primary Examiner*—William E. Kamm
*Attorney, Agent, or Firm*—Dellett, Smith-Hill and Bedell

[57] ABSTRACT

A method for providing an image of the human heart's electrical system derives time-of-flight data from an array of EKG electrodes and this data is transformed into phase information. The phase information, treated as a hologram, is reconstructed to provide an image in one or two dimensions of the electrical system of the functioning heart.

11 Claims, 7 Drawing Sheets

HEART IMAGING METHOD

BACKGROUND OF THE INVENTION

The present invention relates to a method of investigating the proper functioning of the human heart, and particularly to a method providing an image of the heart's electrical system.

Various non-invasive methods are available for viewing portions of the human body, such as X-ray technology, ultrasound, electromagnetic scanning and the like, and in general can provide an image of anatomical shape. Frequent use is also made of electrocardiographic or EKG data for the purpose of ascertaining the physical condition of the human heart. A skilled physician is able to determine considerable information about the heart's operation from the electrocardiographic signal since various portions of the EKG waveform are indicative of the functioning of various components of a heart's anatomy. EKG signals, even though they may be detected at a number of diverse locations on the body, are each responsive to the heart's generalized electrical output, without bearing a specific relation to the location in the electrical pathway of the heart where these electrical signals may be said to originate. Therefore, although the EKG signal is obviously very useful, it is believed further information for diagnostic purposes can be provided through generation of a map of the heart's electrical system in operation. In the instances when disease alters the equivalent shape of the heart's electrical network, it would be helpful to observe a representation of this condition in comparison to an image characterizing a normal heart.

SUMMARY OF THE INVENTION

In accordance with the present invention the electrical system of the human heart is electroholographically imaged by first receiving heart generated electrical (EKG) impulses at a plurality of locations on the patient's body. The relative phase of these impulses is determined according to their reception times, and an image is reconstructed of the heart's electrical system by employing linear impulse holography. In accordance with an embodiment of the invention the impulses are received at a linear array of electrodes. The relative phase information is determined with respect to a time reference to provide data holographically representative of the electrical source configuration transmitting the impulses.

It is accordingly an object of the present invention to provide an improved diagnostic technique for cardiac diseases and the like.

It is another object of the present invention to provide an improved, non-invasive technique for imaging the electrical system of the human heart.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DRAWINGS

FIG. 1 is a schematic illustration of propagation of electrical signals from a point in a patient's heart to a receiving array of electrodes on the patient's chest-abdominal surface, FIG. 2 is a block diagram of a data acquisition and display system employed in accordance with the method of present invention, FIG. 3 is a schematic diagram of pulse-receiving array geometry as used to determine constants in the practical method according to the present invention, FIG. 4 is a diagram of the heart's conduction system, FIG. 5 is a graph illustrating a typical electrocardiographic (EKG) waveform as may be derived in a conventional manner from a human patient, FIG. 6 is a schematic illustration of the production of electrocardiographic (EKG) waveform via a single electrode on the patient's body, FIG. 7 is a waveform chart illustrating a predicted waveform at the detecting electrode in FIG. 6 in response to scanning dipole movement, FIG. 8 is a three-dimensional or perspective view of wave propagation schematically representing dipole movement along the heart's conductive path, FIG. 9 is a waveform chart plotting time-of-flight information as produced by the FIG. 2 circuit, FIG. 10 is a plot of a Fresnel zone phase pattern corresponding to the time data of FIG. 9, FIG. 11 is a linear holographic reconstruction of the image based on the Fresnel zone phase pattern illustrated in FIG. 10, FIG. 12 is a chart illustrating electroholocardiography sampling geometry relative to the human body, and FIG. 13 is an illustration of electroholocardiographic line reconstruction superimposed upon the outline of the patient's heart.

DETAILED DESCRIPTION

Figure 1:
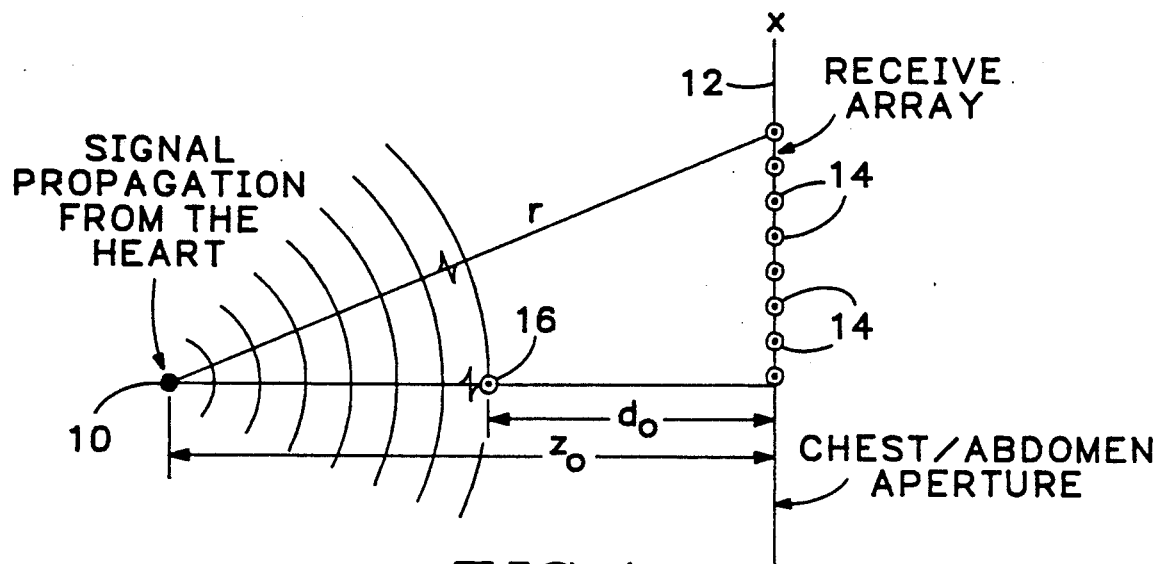

Referring to FIG. 1, electroholocardiographic principles are illustrated in simplified form. Point 10 represents the heart's sinoatrial node (S-A node) emitting a pulse of electrical energy during systolic/diastolic phases. The signal propagates in all directions in the surrounding tissue and can be sampled at the external chest/abdomen surface indicated at 12. A linear array of receiving electrodes 14, closely spaced on the chest/abdomen surface of the patient, receive electrical signals in a manner substantially similar to the way a conventional EKG signal is received. In this drawing, $Z_O$ represents the distance from the heart's S-A node to the chest/abdomen surface and $d_O$ represents the distance from a reference electrode 16 to the surface 12. Reference electrode 16 is another electrode in the general vicinity of electrodes 14.

According to the method of the present invention, the relative phase of the received pulse at each of the electrodes 14 is determined. A "hologram" is then formed and reconstructed into an image that corresponds to the shape of the heart's equivalent, low frequency electrical source.

As will be understood by those skilled in the art, a hologram in the optical sense is formed by light from a source and light from an object that interfere to produce the hologram. The image of the original object can be formed from the hologram in combination with a reconstruction beam similar in nature to the original reference. In the present instance, where electrical signals are utilized rather than light signals, the "reference" is supplied by electrode 16 and is employed to determine the relative phase of the signals respectively received at electrodes 14. (For most purposes, the reference electrode could alternatively comprise one of the electrodes 14.)

Figure 2:
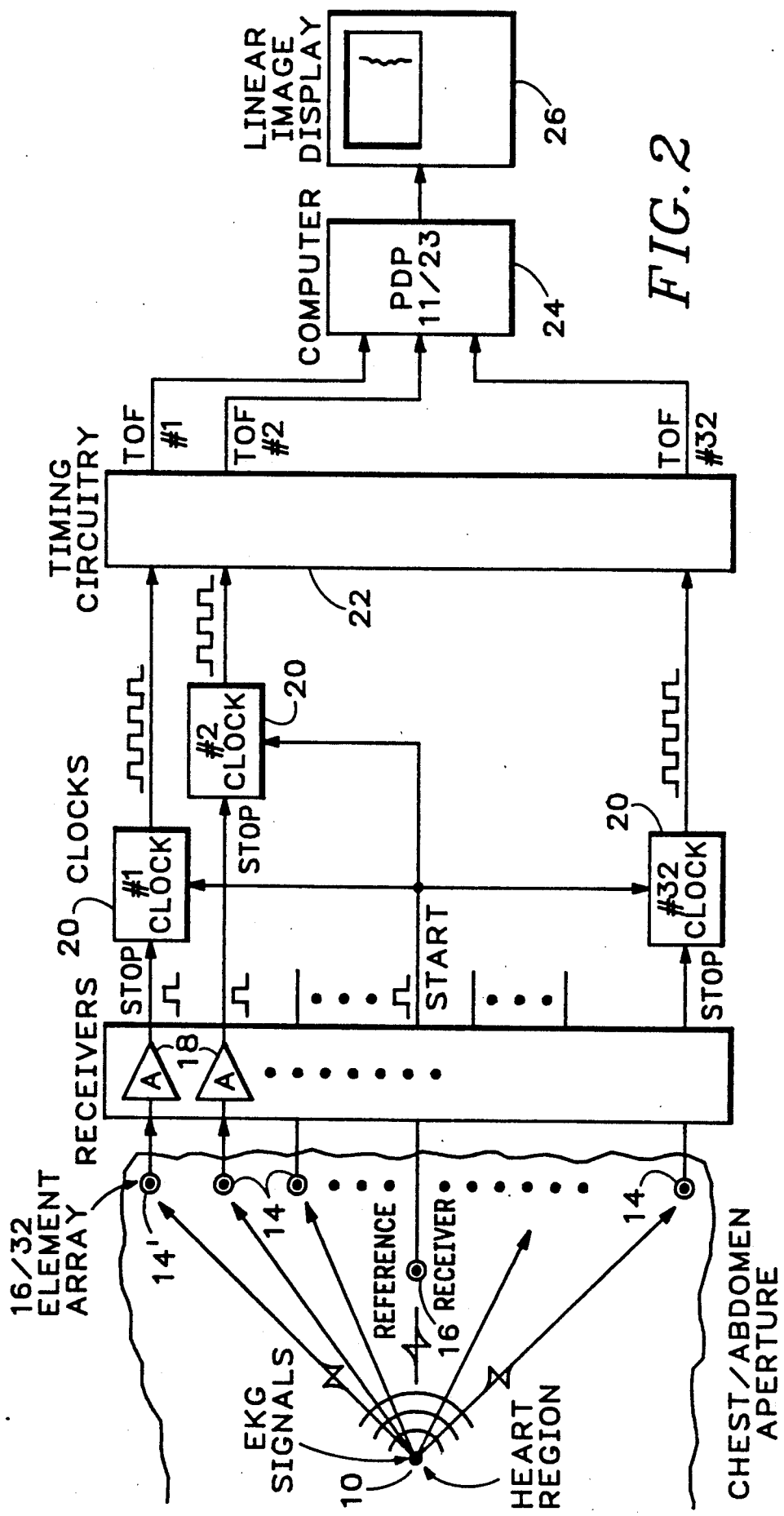

Referring now to FIG. 2, comprising a block diagram of a data acquisition system, the electrical signal from the S-A node 10 is again illustrated as propagating in linear fashion to the array of electrodes 14. Each of the electrodes 14 is connected to a respective receiver in the form of an amplifier 18 which provides an output for stopping a respective clock 20, started by the reference signal received from electrode 16. Each clock 20 thereby supplies an output pulse train having a duration equal to the difference between the time of reception of an EKG impulse at electrode 16 and the time of reception of an impulse at the particular electrode 14 corresponding to that particular clock. Timing circuit 22 generates a numerical output identifying this time difference. The first output, TOF #1, is a time-of-flight signal representing the difference in time between the reception of an EKG impulse at electrode 16 and the reception of the EKG impulse at the uppermost electrode (14') in FIG. 2.

There are 16 to 32 electrodes 14 disposed in substantially linear array on the chest or abdomen of the patient and in close spaced relation to one another. Alternatively, 16 such electrodes may be employed while interpolation is made therebetween by timing circuit 22 for in effect supplying 32 TOF outputs. Such an arrangement allows for effective close spacing between electrodes 14 or their equivalent signals. Of course, the specific number of electrodes mentioned is by way of example and a greater or lesser number may be utilized if desired. A profile of the time-of-flight signals is similar to the curve illustrated in FIG. 9, wherein it will be seen the signals received more centrally from the array exhibit shorter times-of-flight than those received farther out, since the central electrodes are closer to the source.

The 32 TOF (time-of-flight) signals in this particular example are supplied to a computer 24 for calculating the relative "phase" of each of the impulses received. Referring again to FIG. 1, the data are defined by equation (1) which relates the time-of-flight in terms of the average propagation velocity and the EKG signal emission to array element distance:

$$TOF = [1/v_p] [r_i - (Z_O - d_O)] \quad (1)$$

where $r_i = [Z_O^2 + X_i^2]^{\frac{1}{2}}$, $v_p$ = average propagation velocity, $r_i$ = the distance between source 10 and a particular electrode 14 in array 12, and $X_i$ = the distance along the array 12 to the particular electrode 14 to which the radius $r_i$ is drawn, from an origin point on the x axis directly in line with source 10 and electrode 16 in FIG. 1.

It is now intended that a linear hologram be constructed which can then be reconstructed to provide an image of the source. Holography is based upon the measurement of phase rather than pulse transit time. The profile of the TOF signal outputs from timing circuitry 22 is changed to phase information by the conversion, $$\phi = wt \quad (2)$$

where w = radian frequency. A plot of equation (2) yields a profile of the TOF signal outputs from circuitry 22 that would also correspond to the curve shown in FIG. 9. However, if the cosine and sine are then taken, the results are $$f_c(x) = K \cos wt \quad (3)$$
$$= K \cos w(1/v_p)[(X_i^2 + Z_0^2)^{\frac{1}{2}} - (Z_0 - d_0)],$$

and $$f_s(s) = K \sin wt \quad (4)$$
$$= K \sin w(1/v_p)[(X_i^2 + Z_0^2)^{\frac{1}{2}} - (Z_0 - d_0)]$$

Figure 10:
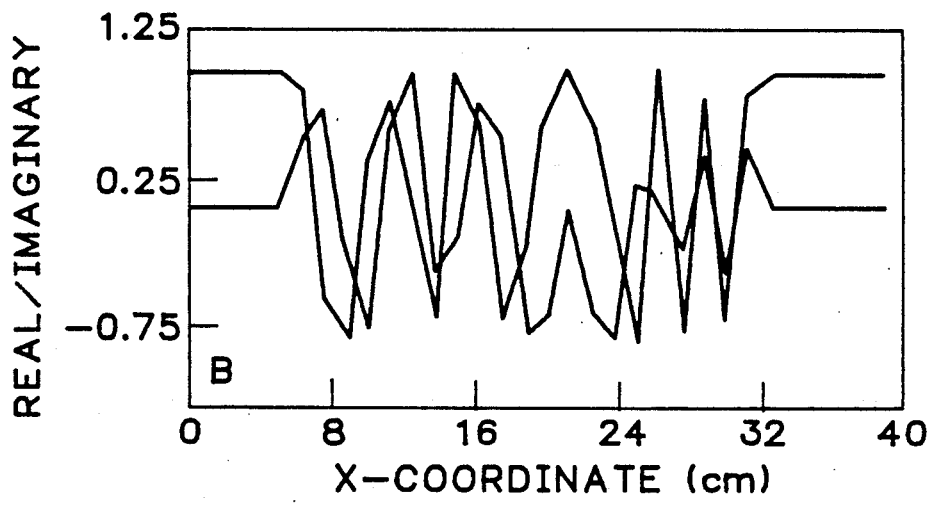

Plots of these functions, which are similar to the curves of FIG. 10, are equivalent to Fresnel zone patterns. As is well known, such a pattern forms the foundation for holography, and if embodied as intensity patterns and presented to a collimated coherent light wave, such patterns would focus to a point.

By signal processing the TOF data, the data may also be converted to holographic format non-optically for the purpose of image reconstruction. A reconstructed result is similar to the curve illustrated in FIG. 11 comprising a linear, holographic reconstruction of the original image based upon the Fresnel zone phase patterns shown in FIG. 10. The curves depicted in FIGS. 9, 10 and 11 were taken with respect to the electrical system of a human heart, rather than a specific point source, and will be referenced subsequently in this specification. However, they aptly illustrate the function of the circuitry of FIG. 2.

The choice of "w" in the equations (2), (3) and (4) to establish a "synthetic" operating frequency is not entirely arbitrary. (See below.) However, having selected the synthetic frequency as a constant, computer 24 in FIG. 2 implements equations (3) and (4) to provide corresponding to the Fresnel zone phase patterns illustrated in FIG. 10, based upon the time-of-flight profile (of FIG. 9). Then, a reconstructed "image" is formed by means of the backward wave propagation (BWP) algorithm, rather than by diffraction of light as in conventional holography. (See "Linear Impulse Holography" by Hildebrand et al, *Acoustical Imaging, Vol. II*, Plenum Press, New York, NY 1982.) The resulting reconstruction is suitably displayed on device 26, comprising a cathode ray tube monitor or the like, such reconstruction corresponding generally to the plot depicted in FIG. 11.

As noted above, the choice or selection of synthetic frequency and EKG sample spacing (the equivalent spacing between electrodes 14) is not completely arbitrary, but rather depends on three parameters: pulse bandwidth, propagation velocity, and source-to-hologram distance. With pulse systems, the timing accuracy (i.e., detection jitter) is a function of the pulse bandwidth (B) or rise time T. Typically, the resultant time jitter in pulse detection systems is about one-hundredth of the rise time (i.e., 0.01 T). The propagation velocity multiplied by the detection jitter is the associated position error in the TOF measurements. These two parameters are involved in an expression for the minimum selectable sample spacing. The source-to-array distance determines the time delay or phase between array samples. The greater the distance, the less time delay between elements. (If the point source were at infinity, a plane wave would exist across the array, i.e., with no time variation and would not be useful for present purposes.)

Figure 3:
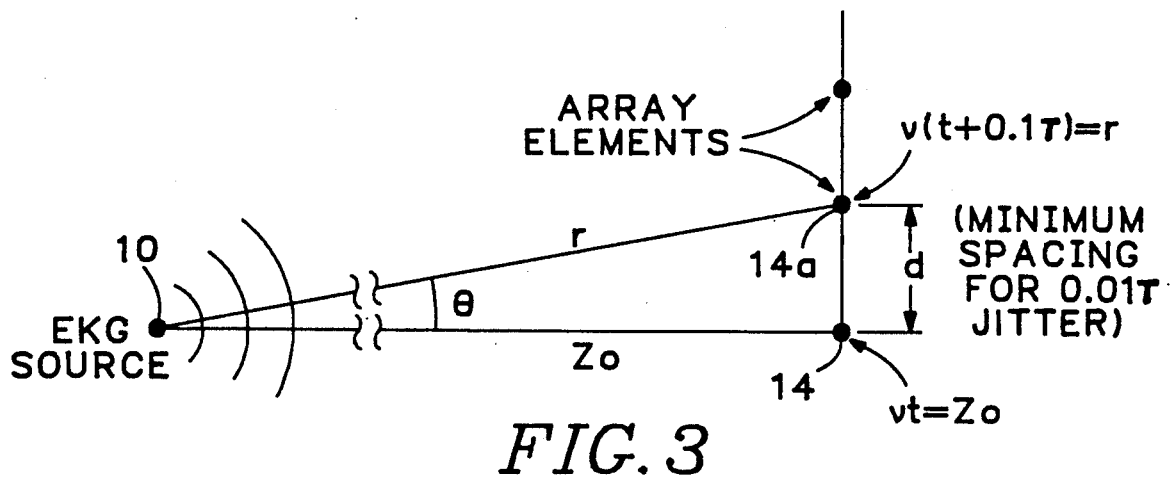

Referring to FIG. 3, illustrating the EKG pulse receiving array geometry used in this analysis, the approximate source-to-array distance for an element 14 is $$r = Z_O + d^2/2Z_O \quad (5)$$

where d = array element spacing for electrodes 14, with r being the distance from the source 10 to a particular electrode 14a.

The minimum detectable time difference between elements is assumed to be 0.01T, and the following equation defines the relationship mathematically $$v_p(0.01T) = d^2/2Z_O \quad (6)$$

where T is the pulse rise time and equals 0.35/B, B being the pulse bandwidth. The array sample spacing d can then be determined as follows:

$$d \geq 0.08 \, [(Z_O v_p)/B]^{\frac{1}{2}}. \quad (7)$$

Also, according to sampling theory, $$d \leq \lambda/2 \quad (8)$$

and the selectable frequency, $$f \leq 6.25 \, ](v_p B)/Z_O]^{\frac{1}{2}} \quad (9)$$

In a typical situation employing EKG data from a human patient, $Z_O = 0.05$ m, B = 20 Hz, and $v_p = 5$ m/sec. The velocity for these EKG signals is noted to be substantially less than the speed of light. Thus, the velocity in the tissue media comprising muscle fibers is less than in nerve fiber, and applicants believe this to be of substantial advantage in being able to provide the electroholographic reconstructed image according to the present invention.

Referring to expressions (7) through (9), above, and utilizing the above described typical parameters, a calculated EKG sampling spacing was approximately one cm, and the maximum selectable frequency, f, was 250 Hz. In a particular example of operation in accordance with the method of the present invention, a synthetic frequency of 195 Hz was selected with a practical sample spacing of 1.27 cm.

The EKG signal source can be "located" within the media, i.e., the human body, by sequential image reconstruction for different depths. The predicted depth or range is then determined by where the optimum "focus" occurs, i.e., for obtaining the maximum amplitude for the line reconstruction of the type illustrated in FIG. 11. The source location algorithm is substantially the same as described in Collins et al, U.S. Pat. No. 4,531,411 issued July 30, 1985.

The lateral resolution for imaging can be calculated using the Rayleigh criterion for incoherent radiation, $$\Delta X = (\lambda Z_O)/L \quad (10)$$

where $L = (m-1)d$ is the array length, $\lambda$ = the wavelength, $Z_O$ = object-to-array distance, and m = number of array elements. Equation (10) can be expressed in terms of array parameters m and $Z_O$ as follows $$\Delta X = 2Z_O/(m-1) \quad (11)$$

where $d = \lambda/2$. Using the EKG data described above, equation (11) yields a lateral resolution of 3.33 mm.

Figure 4:
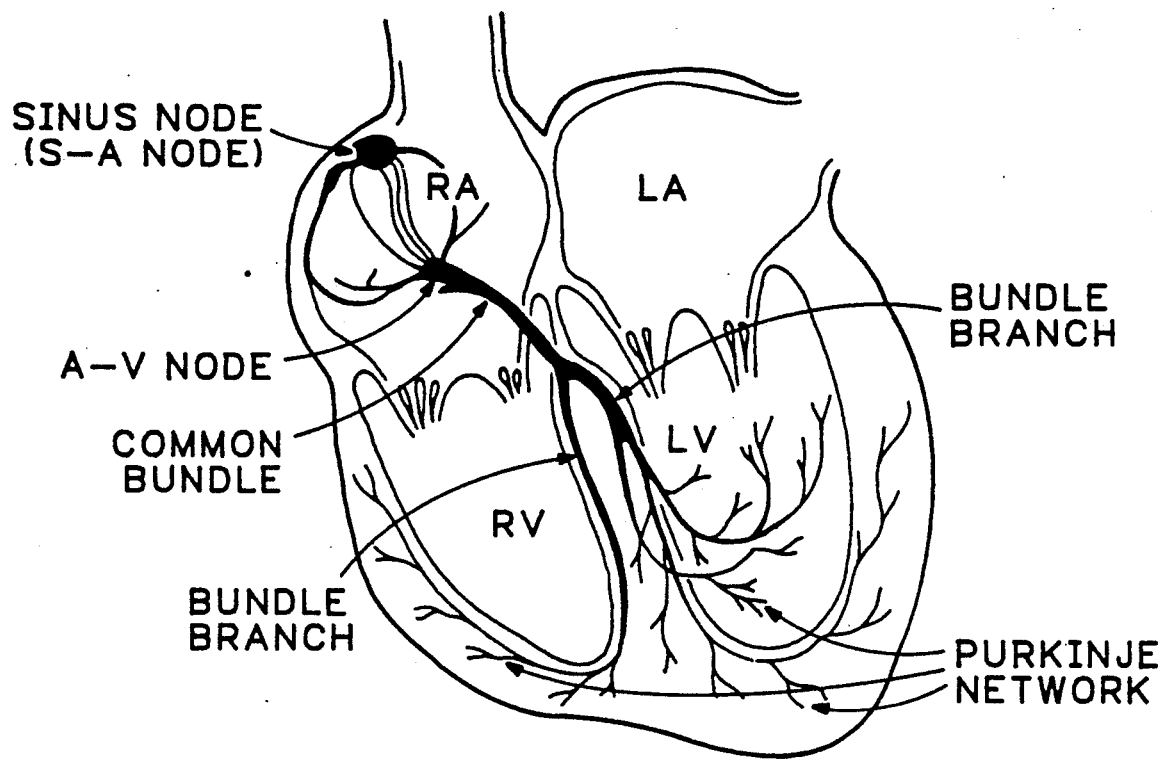
Figure 5:
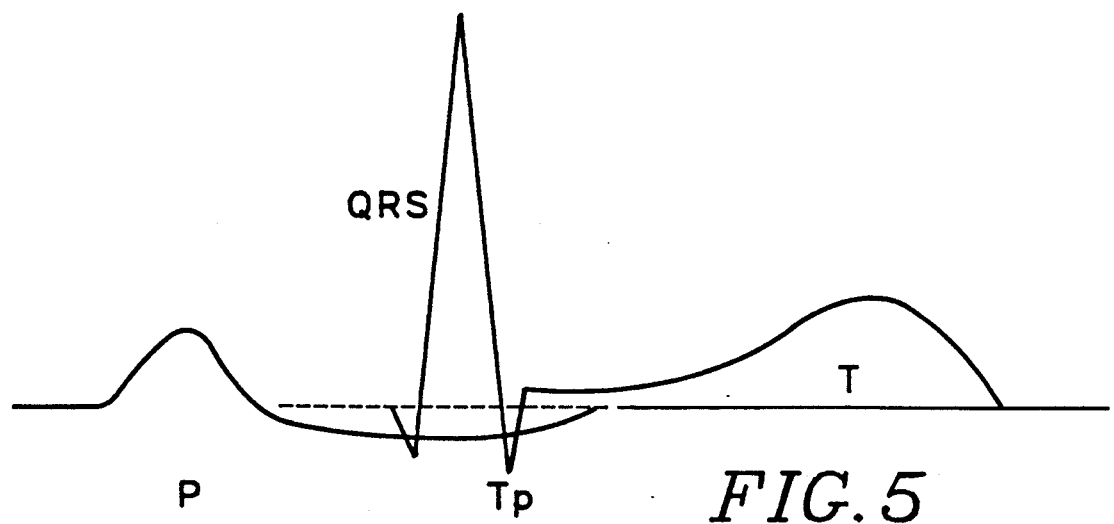

Further considering the physiology of the conduction system of the human heart, reference is made to FIG. 4. The signal generator or clock that generates electrical signals in the heart has its origin in the sino-atrial node (S-A node). From the S-A node, the activation process spreads through both atria. The P wave of the typical electrocardiogram (see FIG. 5) represents atrial depolarization, while repolarization of the atria is designated by the Tp wave which is not ordinarily seen because it is buried in the QRS complex.

After traversing the atrial system, the electrical signal travels to the atriaventricular node (A-V node). It then continues along the common or A-V bundle which penetrates the central fibrous body of the heart and then toward the aortic valve where it bifurcates into left and right bundle branches. These branches separate into smaller subdivision branches that merge into Purkinje fibers. The P-R interval represents the time required for the electrical impulse to travel from the S-A node to the ventricles and is the combination of the atrial, A-V nodal, and His-Purkinje conduction times. The QRS interval represents the intraventricular conduction time, normally being 60 to 100 ms. Ventricular repolarization is represented by the T wave.

Figure 6:
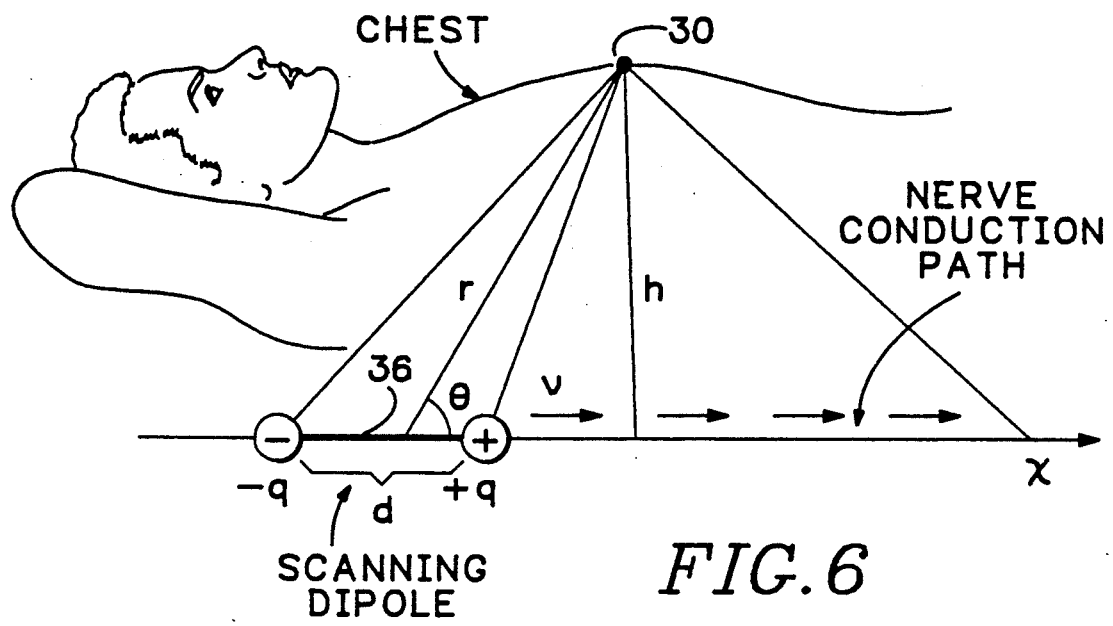
Figure 7:
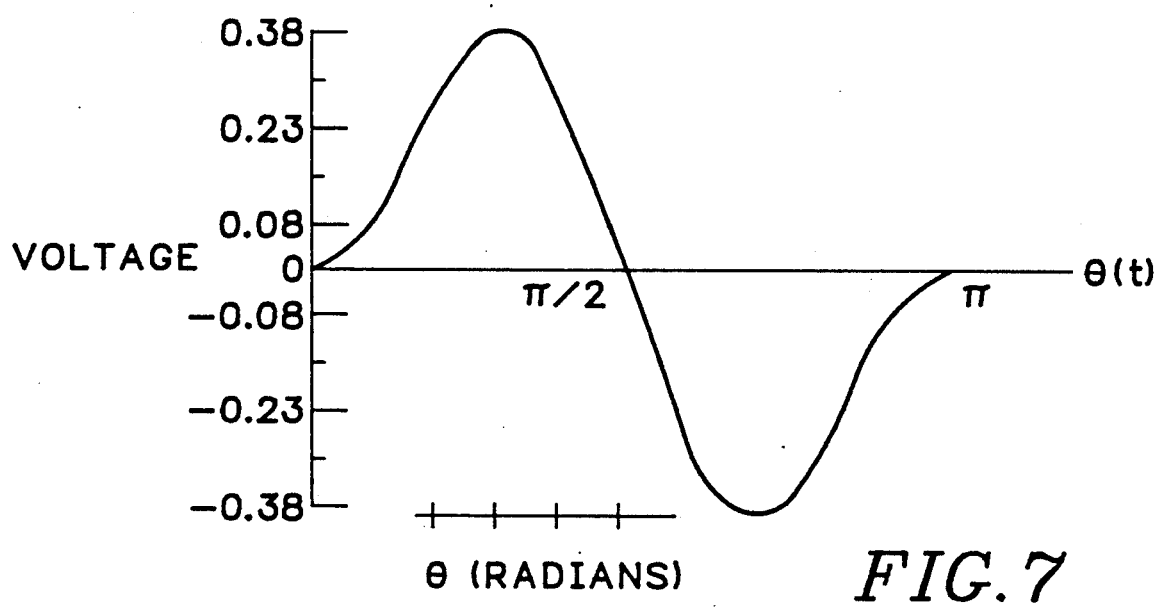

A simple approach to the electrophysiology of the heart is to consider the electrical properties of individual cardiac muscle fibers. When a muscle strip is at rest, or in the polarized state, a series of positive charges lines the outer surface of a cell membrane, and a corresponding number of negative charges line its inner surface. Each pair of positive and negative charges is called a dipole. Stimulation of the muscle cell causes the electrical resistance to decrease at the site of stimulation, and the process may then be represented by a series of dipoles consisting of positive charges in advance of negative charges traversing the cell surface from the stimulation site to the opposite end of the cell. For convenience, an entire series of dipoles may be represented by a single equivalent scanning dipole. Thus, the conduction, depolarization sequence may be simulated by a scanning electrical dipole initiated in the S-A node and then traveling throughout the conduction system of the heart. FIG. 6 is a simple dipole model and FIG. 7 is a predicted impulse waveform (similar to a QRS signal) produced as the aforementioned dipole, 36 in FIG. 6, is assumed to progress along the conduction path, i.e., from left to right. Of course, this model is only an approximation of what actually happens, but is believed useful in understanding the electrical principles involved.

According to electromagnetic field theory, the potential at the receiving point, i.e., at a conventional EKG probe electrode 30 in FIG. 6 located on the external chest surface, is approximately given by the following expression:

$$V[\phi(t)] \sim [(gd)/(4\pi E h^2)] \cos\phi(t) \sin^2\phi(t) \quad (12)$$

where g = dipole charge, d = dipole charge separation distance in m, E = dielectric constant and $\phi(t)$ = scanning angle between the dipole axis and the EKG receiving point 30.

The waveform $V(\phi(t))$, as illustrated in FIG. 7, is generated as the scanning dipole travels along the conduction path in the positive X direction, i.e., from left to right in FIG. 6, and $\phi(t)$ essentially varies from zero to $\pi$ radians. The waveform as illustrated in FIG. 7 is a plot of equation (12) and is roughly similar to a QRS signal of the EKG waveform.

Figure 8:
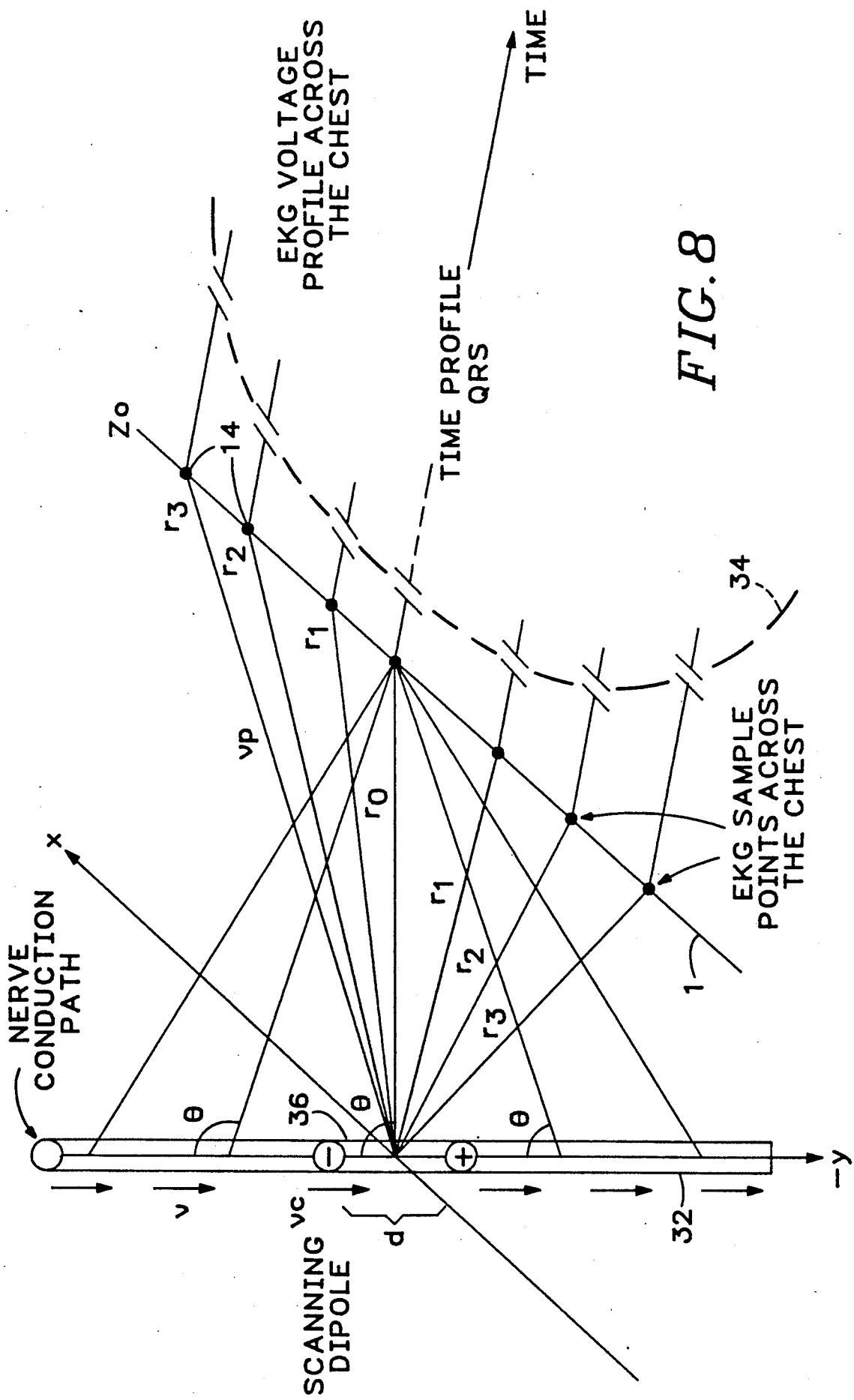
Figure 9:
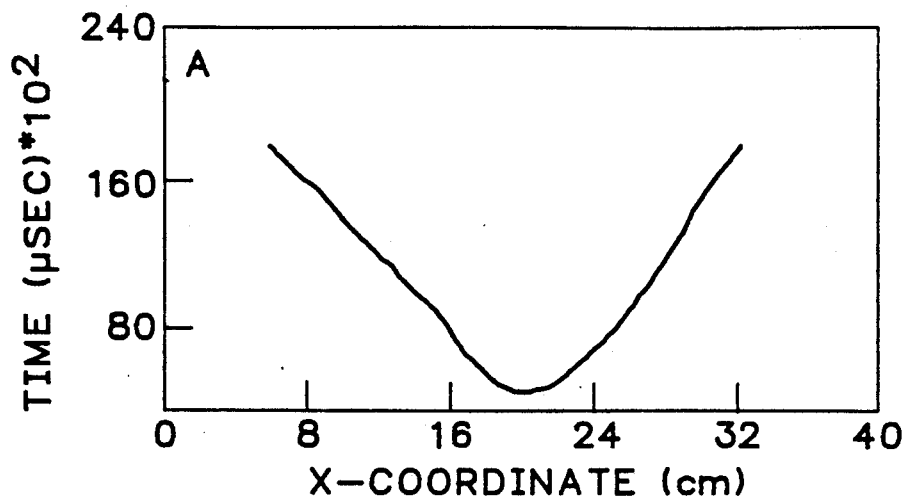

The effect of this postulated scanning dipole can be described in conjunction with an array of electroholocardiographic electrodes 14 disposed in the chest/abdomen region of a patient. With reference to FIG. 8, indicating the heart's main conduction path 32 in the vertical direction, an array of electrodes 14 is placed across the chest of the patient, i.e., in substantial juxtaposition with the heart but extending crossways of the heart's vertical conduction path 32. The resulting profile of the time-of-flight signals is also illustrated graphically at 34. This time-of-flight profile, corresponding to that illustrated in FIG. 9, depicts longer time-of-flight measurements for electrodes at progressively longer distances, $r_1$, $r_2$ and $r_3$, from the scanning dipole 36. The profile 34 of the received signals thus represents increased delay times as the observation point is farther from a central position (i.e., that for ray $r_o$), and resembles a typical point source TOF curve.

The diagram of FIG. 8 can be used to visualize wave propagation as the scanning dipole traverses the nerve conduction path 32 with a velocity $v_c$ in the negative "Y" direction (downwards in FIG. 8). The propagation model of FIG. 8 is similar to observed phenomena, with apparent substantial equivalence between a scanning dipole and a point source.

Figure 12:
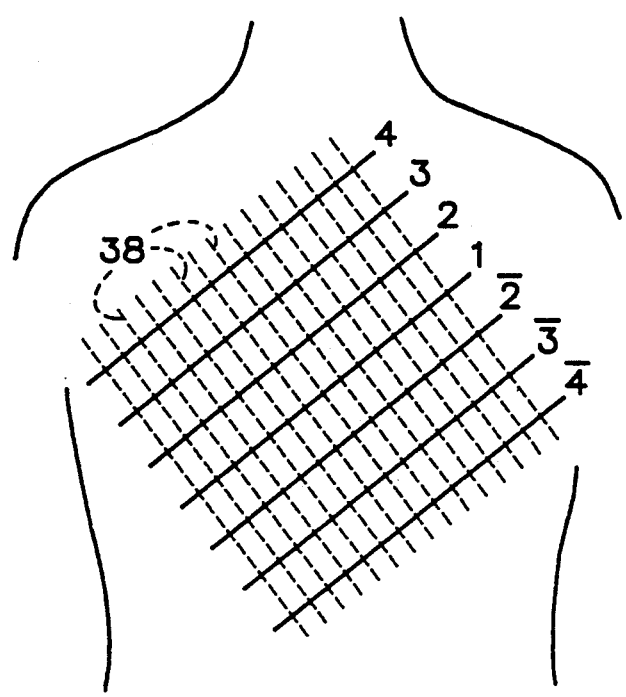

In a typical example of the generation of reconstruction information representative of the electrical system of the human heart, several parallel line arrays of sensors, designated 4, 3, 2, 1, 2, 3 and 4 in FIG. 12 were disposed across the chest of a patient in a direction more or less orthogonal to the assumed main conduction path of the heart, such path running at an angle of approximately 50° from the vertical axis of the human body. (See FIG. 13.) Parallel dashed lines 38 extend generally parallel to the main electrical pathway of the patient's heart while the intersections between dashed lines 38 and array or "scan" lines 4 through 4 denote locations of respective impulse receiving electrodes. In accordance with an aspect of the present invention, successive scan lines form "apertures" which, considered together, present a view of the heart's electrical system in two dimensions.

Figure 11:
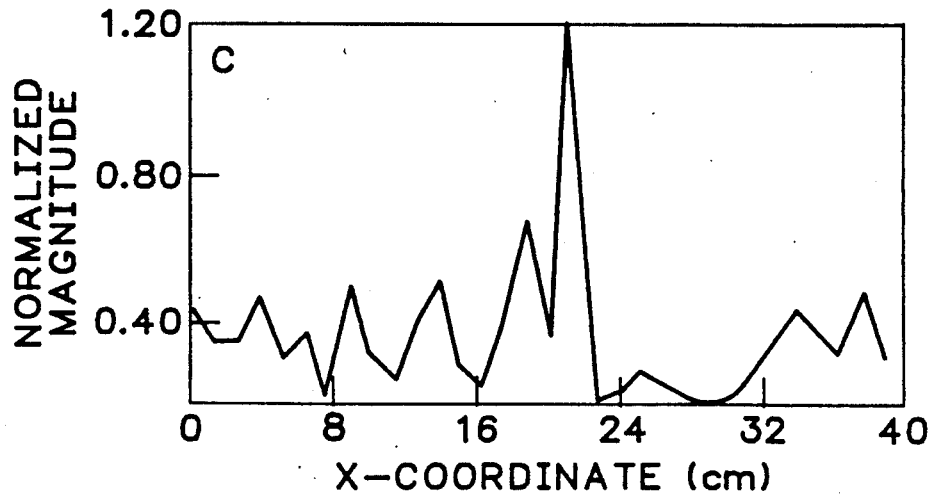

FIGS. 9, 10 and 11 are plots of data taken from a human patient provided with an array of receiving electrodes disposed along a line adjacent and parallel to scan or array line 1 in FIG. 12. The time-of-flight curve in FIG. 9 profiles the various times at which the heart generated impulse is received at respective electrodes corresponding to electrodes 14 schematically illustrated in FIG. 8. The time-of-flight curve was generated from sixteen discrete sample points with sixteen additional interpolated points making a total of thirty-two points with a sample density of 1.27 cm. As will be recognized by those skilled in the art, the curve is similar to the typical time-of-flight curve as would be generated for a single point. FIG. 10 plots the Fresnel zone patterns, both real and imaginary, computed from the time-of-flight profile using a selected synthetic frequency (195 Hz in this case), according equations (3) and (4) above. FIG. 11 is the linear reconstruction of this holographic data. The alignment of the scan or array axis approximately perpendicular to the heart's major nerve conduction path generates essentially one central point and several lesser network paths viewed for adjacent areas of the heart.

Figure 13:
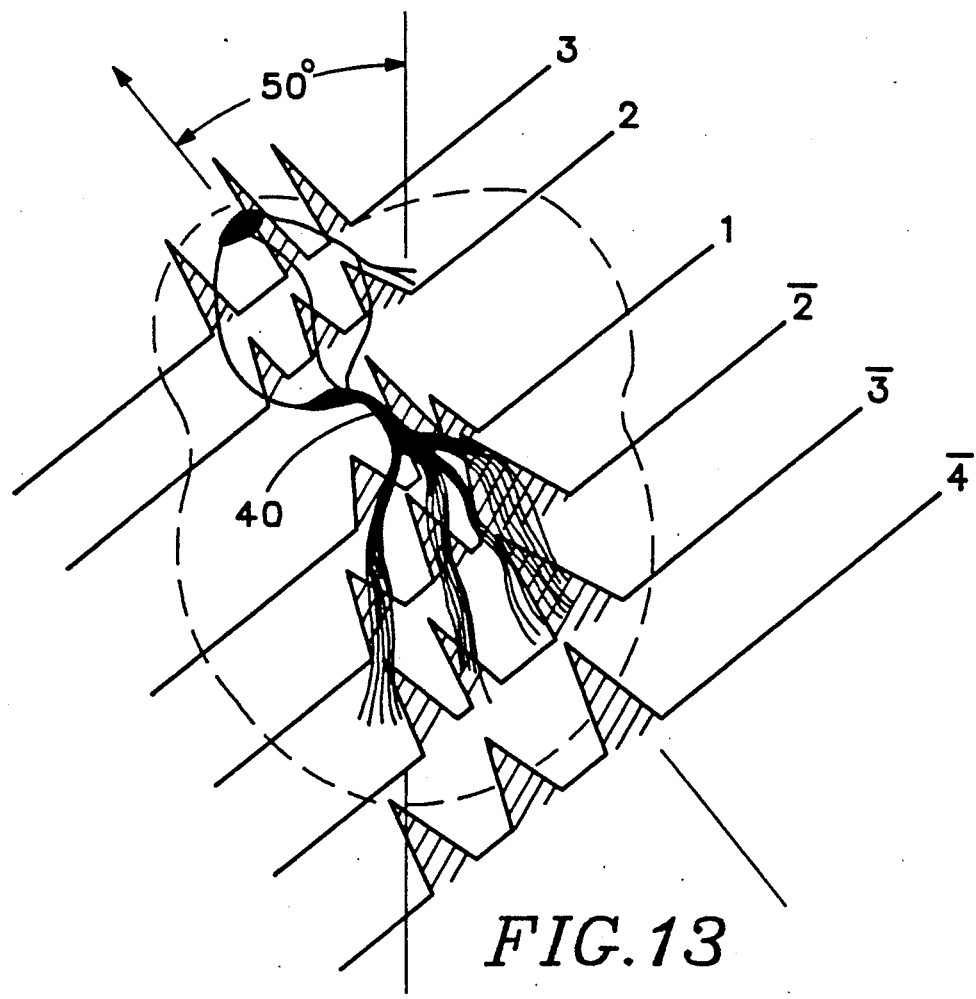

In FIG. 13 a schematic representation 40 of the conduction system of the heart has superimposed thereover several line image reconstructions generated from time-of-flight information gathered via similarly numbered arrays of electrodes illustrated respectively in FIG. 12. Considerable similarity will be observed between the linear constructions and the heart's conductive network cross-section successively represented thereby.

According to the present invention a unique holographic image is generated defining the equivalent geometrical shape of the heart's low frequency nerve conduction network. If disease should alter the source network's equivalent shape, this can be detected in either the hologram or the reconstructed image. The method is a unique passive, non-invasive diagnostic technique for providing the physician with information on the functioning heart not heretofore available.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of depicting data relating to a patient's heart, comprising:
   receiving heart generated impulses at a plurality of locations on the patient's body,
   determining relative phase information from ones of said impulses as received, according to their respective times of reception at said plurality of locations, and
   reconstructing an image of the electrical system of said patient's heart from said phase information.

2. The method according to claim 1 wherein receiving heart generated impulses at a plurality of locations on the patient's body comprises providing an array of electrodes on the patient's body and receiving said impulses at said array of electrodes.

3. The method according to claim 1 wherein determining relative phase information from ones of said impulses as received, according to their respective times of reception, comprises determining relative phase information with respect to a time reference for providing data holographically representative of a source configuration transmitting said impulses.

4. A method of imaging the electrical system of a patient's heart, comprising:
   receiving heart generated electrical impulses at closely spaced locations upon said patient's body, in proximity to the patient's heart,
   determining time-of-flight data for said electrical impulses at said spaced locations, said time-of-flight data being defined relative to a reference location,
   converting said time-of-flight data into phase data holographically representative of the electrical source configuration transmitting said impulses, and
   reconstructing an image of the electrical system of said patient's heart from said phase data.

5. The method according to claim 4 wherein receiving heart generated electrical impulses at closely spaced locations upon said patient's body, in proximity to the patient's heart, comprises providing an array of electrodes, and including disposing said electrodes approximately linearly and orthogonally to the main electrical pathway of the patient's heart for reception of said impulses at said array of electrodes.

6. The method according to claim 5 further including providing further linear electrode arrays generally parallel to the first mentioned array, receiving said impulses at said further arrays, and processing data therefrom to provide further reconstructed images substantially parallel to the first to provide an overall representation in two dimensions.

7. The method according to claim 5 wherein determining time-of-flight data for said electrical impulses at said spaced locations comprises measuring time-of-flight data for each electrode by clocking the elapsed time required for said electrical impulses to reach each said electrode relative to at time reference, and wherein said time reference is provided by locating a reference electrode proximate said array of electrodes and receiving a reference impulse via said reference electrode.

8. The method according to claim 4 further comprising converting said time-of-flight data to phase data as trigonometric functions of times-of-flight multiplied by a synthetic frequency.

9. The method according to claim 8 further comprising determining said synthetic frequency in accordance with the average propagation velocity of said electrical impulses in muscle tissue, pulse rise time, and the distance of the heart's electrical pathway to the surface on the patient's body where the electrical impulses are received.

10. The method according to claim 4 wherein said reconstructing an image of the electrical system of said patient's heart from said phase data further comprises accomplishing said reconstruction according to the backward wave algorithm.

11. A method of generating an image of a heart comprising the steps of:
measuring a plurality of electrical impulses generated by the heart at a plurality of locations on a patient's chest,
determining wave propagation characteristics of ones of said plurality of electrical impulses, and
generating a holographic representation of the electrical system of the heart based on said wave propagation characteristics.

* * * * *

UNITED STATES PATENT AND TRADEMARK OFFICE
CERTIFICATE OF CORRECTION

PATENT NO. : 5,038,791

DATED : August 13, 1991

INVENTOR(S) : H. Dale Collins et al

It is certified that error appears in the above-identified patent and that said Letters Patent is hereby corrected as shown below:

Column 5, line 56, "$\Delta x = (\lambda z_0)/L$" should be
 -- $\Delta x = (\lambda \backslash z_0)/L$ --.

Column 5, line 61, "$z_0$ as follows" should be
 -- $z_0$, as follows --.

Column 7, line 29, "4, 3, 2, 1, 2, 3 and 4" should be
 -- 4, 3, 2, 1, $\overline{2}$, $\overline{3}$ and $\overline{4}$ --.

Column 7, line 37, "4 through 4" should be -- 4 through $\overline{4}$ --.

Column 9, line 13, "at time" should be -- a time --.

Signed and Sealed this

Fourteenth Day of December, 1993

*Attest:*

BRUCE LEHMAN

*Attesting Officer*      *Commissioner of Patents and Trademarks*